United States Patent [19]
Hertzmann

[11] Patent Number: 4,580,557
[45] Date of Patent: Apr. 8, 1986

[54] SURGICAL LASER SYSTEM WITH MULTIPLE OUTPUT DEVICES

[75] Inventor: Peter Hertzmann, Palo Alto, Calif.

[73] Assignee: Laserscope, Santa Clara, Calif.

[21] Appl. No.: 525,833

[22] Filed: Aug. 22, 1983

[51] Int. Cl.$^4$ .............................................. A61B 17/36
[52] U.S. Cl. .................. 128/303.1; 128/395; 219/121 LA; 219/121 LZ
[58] Field of Search ...................... 128/303.1, 395–398; 219/121 LA, 121 LB, 121 LP, 121 LQ, 121 LR, 121 LZ; 372/38, 108, 109

[56] References Cited

U.S. PATENT DOCUMENTS

| | | | |
|---|---|---|---|
| 3,703,176 | 11/1972 | Vassiliadis et al. | 128/303.1 |
| 4,388,924 | 6/1983 | Weissman et al. | 128/303.1 |

FOREIGN PATENT DOCUMENTS

| | | | |
|---|---|---|---|
| 0075912 | 4/1983 | European Pat. Off. | 128/303.1 |
| 2832847 | 2/1980 | Fed. Rep. of Germany | 128/395 |
| 3105297 | 12/1981 | Fed. Rep. of Germany | 128/303.1 |
| 788475 | 9/1981 | U.S.S.R. | 128/398 |

*Primary Examiner*—Lee S. Cohen
*Attorney, Agent, or Firm*—Ciotti & Murashige

[57] ABSTRACT

A surgical laser system includes a laser, interchangeable peripheral output devices, a sensor effective to sense the power output of a peripheral device coupled to the sensor, and a control circuit for calibrating the radiation output of each device, interlocking the system to prevent use of a device before it has been calibrated, and controlling the production of calibration, aiming and main power laser beams.

8 Claims, 7 Drawing Figures

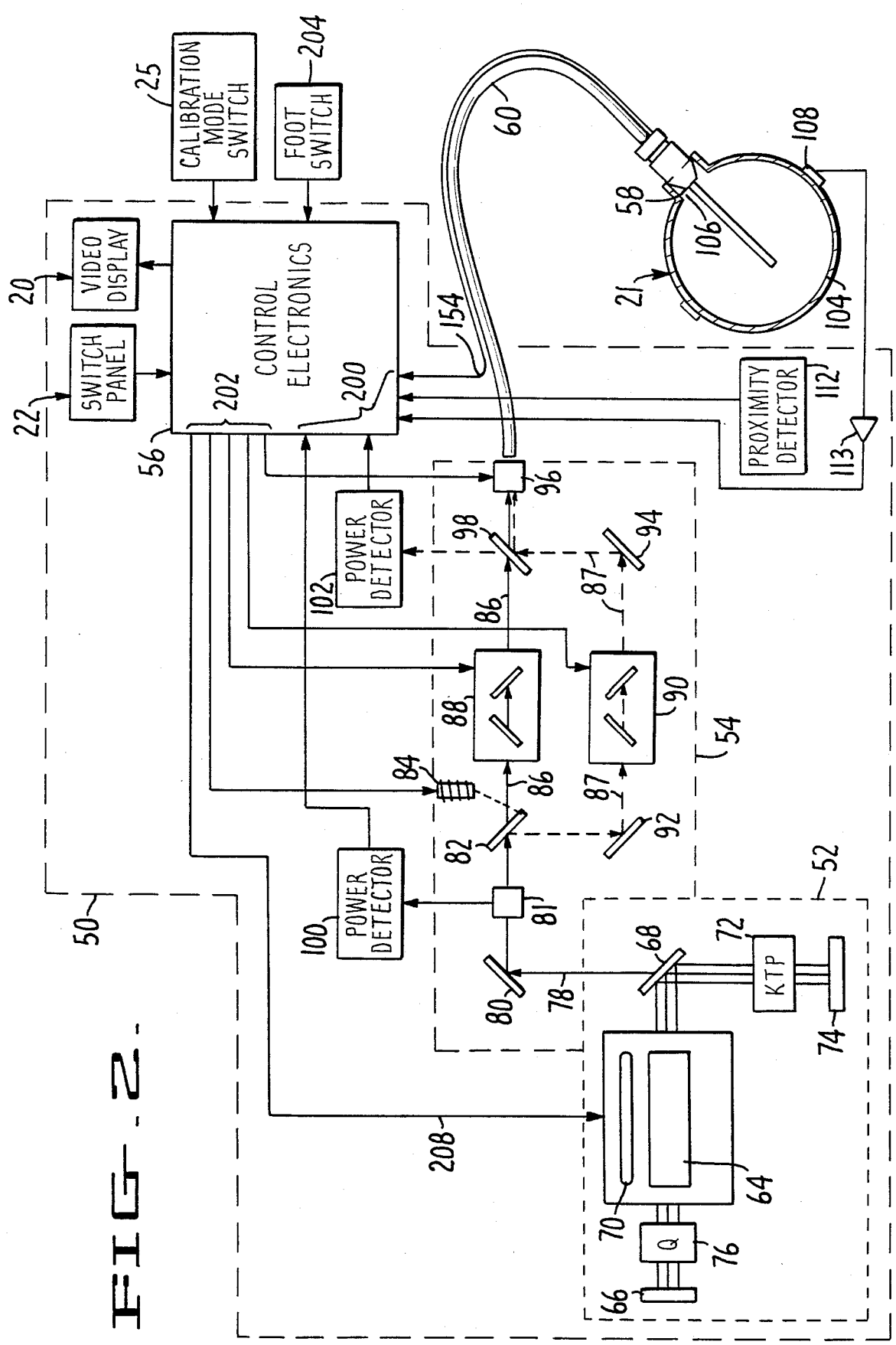

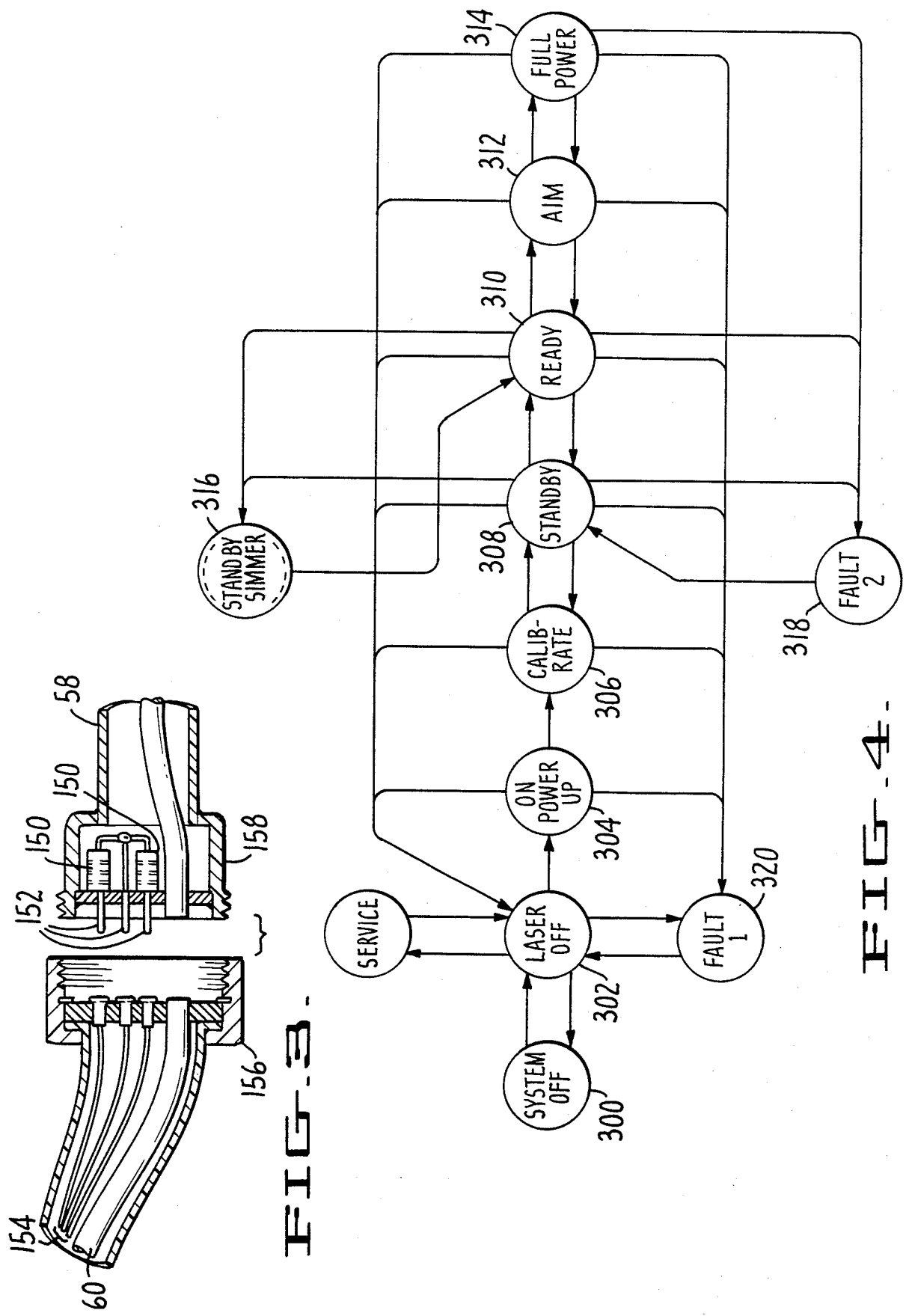

SURGICAL LASER SYSTEM WITH MULTIPLE OUTPUT DEVICES

BACKGROUND OF THE INVENTION

The present invention relates to a system for providing laser radiation for medical or surgical applications.

A number of surgical techniques employing laser radiation have been developed, such as cutting or cauterizing tissues. Various laser beam manipulator devices having been employed as surgical scalpels as illustrated, for example, in U.S. Pat. No. 3,865,113 to Sharon et al. Photo-coagulating devices employing a laser have been employed to effect coagulation in a portion of a patient's eye. See, for example, U.S. Pat. No. 3,487,835 to Koester et al. Laser optical devices, known in the art, may also include provisions for operation under a microscope to perform microsurgery. See, for example, U.S. Pat. No. 4,091,814 to Togo. These various techniques have created a need for medical laser systems having varied power levels and peripheral attachments, so that a single laser may be used in performing these various techniques.

It is necessary to precisely control the amount of laser radiation delivered to biological tissues in photo-surgical procedures. The appropriate amount of radiation is known to vary with the technique employed. Systems have been developed to control the intensity and duration of the laser radiation energy applied to the treated tissues. See U.S. Pat. No. 4,215,694 to Isakov et al and U.S. Pat. No. 4,122,853 to Smith. Systems such as the Smith system rely on exposure control devices such as shutters and laser power level control circuits.

The difficulty of controlling the amount of laser radiation delivered to tissues is aggravated when various peripheral devices, having varying optical properties and power requirements are used in the same system. Moreover, the optical properties and power requirements of a single tool may gradually change due to wear, debris build-up, etc.

Accordingly, it is an object of the present invention to provide surgical laser system and technique for identifying and calibrating various interchangeable peripheral surgical devices before use.

It is another object of the present invention to provide surgical laser systems and techniques, having interlocks to inhibit the use of uncalibrated surgical devices.

It is another object of the present invention to provide a control system for a surgical laser for producing appropriately selected laser radiation dosages from various surgical devices, the radiation being derived from a single laser radiation source.

It is another object of the present invention to provide a surgical laser system having a power beam and aiming beam controlled by a calibrated attenuation system and derived from a single laser radiation source.

It is another object of the present invention to provide displays of calculated system energy output levels based on readings obtained from an interlocked calibration system.

These and other objects and features will be apparent from this written description and appended drawings.

SUMMARY OF THE INVENTION

The present invention relates to novel methods and systems for controlling a medical laser device to provide calibrated radiation output levels and interlock the system against uncalibrated or accidental use.

A laser apparatus, constructed according to the teachings of the present invention, includes a laser and a plurality of peripheral medical output devices adapted to be coupled to the laser to receive laser radiation from the laser. These devices may include laser scalpel, opthalmic photo cautery devices, microsurgical systems, etc. In preferred embodiments of the present invention, such peripheral devices are equipped with identifying signature devices, such as signature resistors, for identifying the device and distinguishing it from other types of devices or others of the same type of device.

The apparatus may also include a radiation sensor, such as the combination of an integrating sphere and semi-conductor photo-detector, for sensing a radiation output of a surgical device selectively coupled to the radiation sensor. This coupling may be effected by inserting a radiation output portion of the peripheral surgical device into the radiation sensor.

The apparatus may include a control circuit for identifying the surgical device currently coupled to the laser, by means of the surgical device signature means. The control circuit may also enable the apparatus to produce a low power radiation output from the surgical device when the surgical device is coupled to the radiation sensor, thereby permitting a calibration reading to be taken for this particular surgical device. The control circuit may also disable the apparatus from producing a radiation output for surgical use until the radiation output of the surgical device has been sensed by the radiation sensor. Thus the control circuit provides an interlock to prevent the use of an uncalibrated surgical device to avoid the possibility that an incorrect amount of laser radiation would be delivered to biological tissues on which surgery is to be performed.

Preferred embodiments of the present apparatus may include a radiation sensor for sensing the radiation output from the laser at a location in the system ahead of the location where laser radiation is coupled to the peripheral surgical device. In this case, the control circuitry may determine and store a value representative of the ratio of the sensed radiation output from the laser to the sensed radiation output of the surgical device when coupled to such radiation output. This ratio may be used as a calibration value for estimating the actual power output of the surgical device when the surgical device is being used to perform surgical procedures.

Provision may be made for manually or electrically entering a power output set-point which represents the power output desired from a particular surgical device to be used. The control circuit of the apparatus may calculate a laser output power level from the power output set-point and from the value representative of the output ratio. A signal related in value to this calculated power level may be used to control the laser.

In embodiments of the present invention, the control circuit may store and recall information concerning the output power ratio. In particular, the information may be recalled responsive to a recoupling of a particular peripheral surgical device to the laser. In such a case, the recalled value may be displayed by the apparatus.

In embodiments of the present invention, the apparatus may include beam directing and attenuating systems for producing a main laser power beam and a lower power aiming beam, and for selectively coupling one of these beams to the surgical device. A two state control switch may be provided, for triggering emission of laser radiation from the peripheral device. In a first state, the emission of the lower power aiming beam is triggered, while in the second state the main beam is triggered. The switch may be interlocked so that the switch is placed in the first state for a predetermined period of time before it may be placed in the second state.

The present invention also embraces methods for effecting the calibration of a surgical laser apparatus which includes a laser adapted to be coupled to various peripheral surgical devices. The method may comprise identifying a peripheral surgical device coupled to the laser by sensing an identifying signature of the surgical device. The apparatus may then be enabled for calibration to produce a radiation output from the surgical device when the surgical device is coupled to a power sensor. The radiation output of the surgical device is then measured with the power sensor, while the radiation output of the laser itself is being measured. Control circuitry of the apparatus may then determine and store a ratio of the aforementioned sensed radiation outputs, the ratio being a calibration value for the particular surgical device being calibrated. When these steps have been performed, the apparatus may be enabled for surgical use to produce a radiation output from the surgical device when the surgical device is removed from the power sensor. Interlock mechanisms may be provided to require that these procedures be repeated to calibrate each of a plurality of peripheral surgical devices to be used. The interlock systems also inhibits the use of uncalibrated peripheral devices, and improperly connected peripheral devices, as well as use of the system with no peripheral device connected.

The system may detect the recoupling to the laser of a surgical device which was previously calibrated. When this occurs, the apparatus may recall the stored calibration value from the surgical device. A desired power output set-point may be entered for the tool and the apparatus may calculate a laser power output level from the calibration value and from the power output set-point for the surgical device. The apparatus may then be enabled to produce radiation for surgical use at the calibrated power output level.

BRIEF DESCRIPTION OF THE DRAWINGS

FIG. 2 is a schematic diagram of an embodiment of the optical and electrical elements employed in the laser system of the present invention.

FIG. 3 is a detail of FIG. 2 showing the construction of connector portions of a peripheral surgical device and a cable emanating from the system console.

FIG. 4 is a schematic illustration of modes of operation of the control circuitry of a laser system embodiment of the present invention.

DETAILED DESCRIPTION

Figures 1, 1A, 1B, 1C:
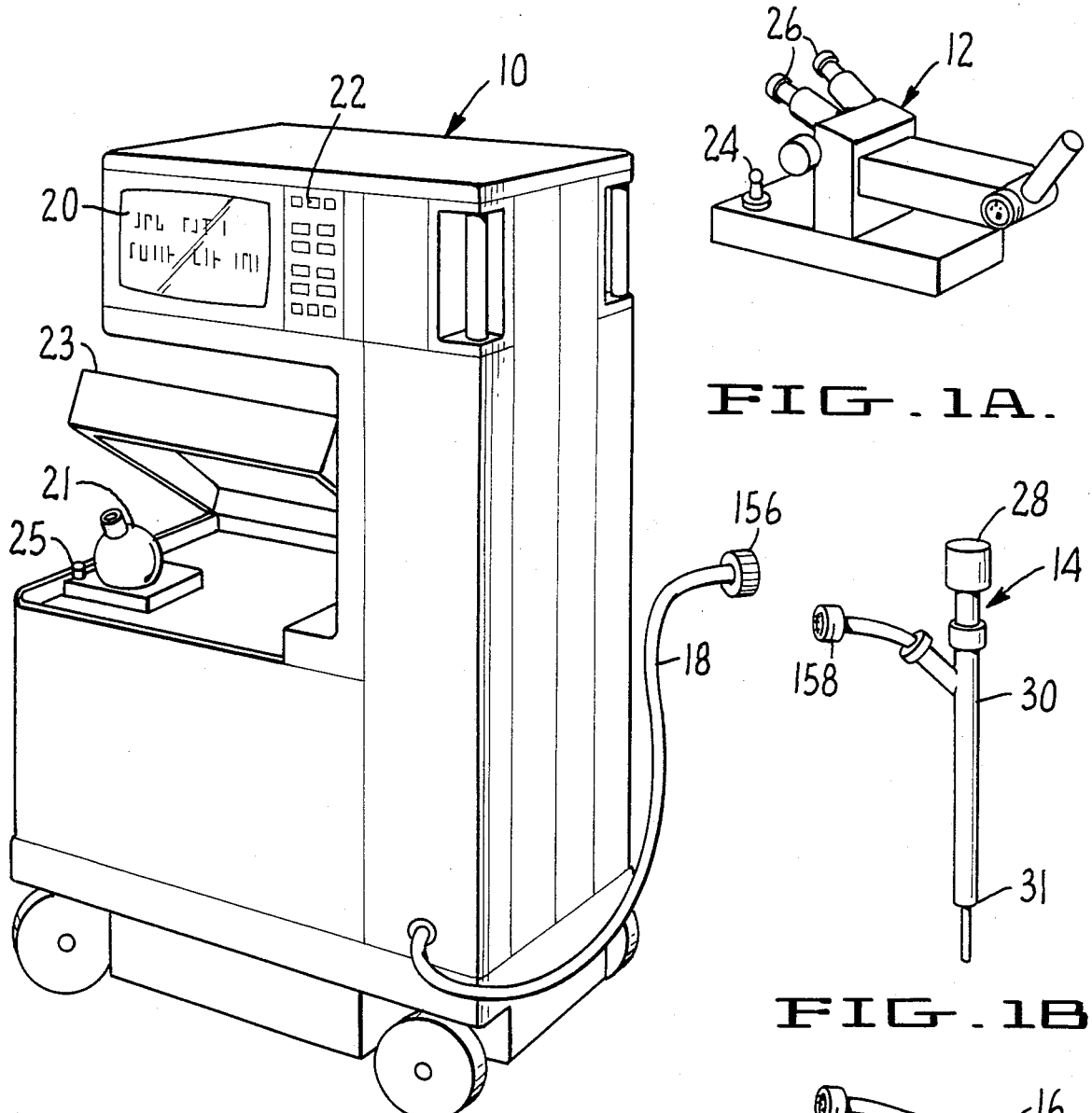
FIG. 1 is a pictorial view of a medical laser system console and examples of peripheral surgical peripheral devices used therewith.

Referring first to FIG. 1, a medical laser system is illustrated including a laser console 10 and several exemplary peripheral surgical devices 12, 14 and 16. The peripheral surgical devices are adapted to be selectively coupled to the console 10 by means of a optical fiber cable 18.

The console 10 may include an optical system consisting of a laser, directing and attenuating devices, and control electronics. These constituents of the system are described in greater detail in connection with FIG. 2.

The console may also include a video display 20 by which the operation of the system is monitored, and a switch panel 22 by which the system may be manually controlled, for example, by entering of power output set points suitable for the particular surgical technique and peripheral device in use.

A calibration pod 21 may be stored in the console 10 under a lid 23. When a peripheral device is to be calibrated, the lid 23 may be lifted and the pod 21 removed thereby placing the system in a calibration mode. The device may then be optically coupled to the pod, and a calibration mode switch 25 actuated to initiate a low power laser pulse employed in the calibration process. This process will be described in greater detail below.

The exemplary peripheral surgical devices shown in FIG. 1 include a combination microscope and laser beam directing system 12 for performing microsurgery. This device may include a joy stick manipulator 24 for directing the laser beam onto tissues observed through the microscope eye pieces 26. Another exemplary peripheral surgical device shown is the laser endoscope 14, which includes an eye piece 28 and optical system 30 for viewing the surgical operation performed through a catheter portion 31 of the device. The third exemplary periphery surgical device 16 is a laser scalpel having a shank portion 32 for manual manipulation and an output tip 34 through which laser light may be directed to tissues for the purpose of cutting the tissues. It should be understood that the examples of peripheral surgical devices shown in FIG. 1 are not exhaustive. Such devices may also include dermal handpieces, microsurgical scalpels, microsurgical handpieces, intraoccular probes, rhinal probes, microcautery probes, macrocautery probes, endoscopic probes, laser microscopic devices, and other laser powered medical devices known in the prior art. They may also include cautery probes and scalpels having tip portions heated by laser radiation, wherein the laser light does not impinge on the tissues. Such devices are described in the patent application of Perkins and Hertzmann, ser. no. G-485480 filed Apr. 15, 1983.

FIG. 2 is a schematic diagram of an embodiment of the optical and electrical elements employed in the surgical laser system of the present invention. The portion of the apparatus which may be enclosed within the console 10 of FIG. 1 is surrounded by the dotted line 50. The apparatus may include a laser 52, a beam directing and attenuating optical system 54 and control circuitry 56. Laser radiation may be coupled to a peripheral surgical device 58 by means of a optical fiber cable 60.

In operation the control circuit may be employed to identify the peripheral surgical device by means of a device signature, enable the apparatus to produce a radiation output from the surgical device when the surgical device is coupled to the radiation sensor 21 for calibration, and disable the apparatus from producing a radiation output for surgical use until the radiation output of the surgical device has been calibrated.

The details of the constructions of the apparatus of FIG. 2 will now be described in detail.

The laser 52 may, advantageously, be a frequency doubled YAG laser. Such a laser is capable of providing relatively high power levels at a frequency or wavelength such that readily available, flexible optical fiber cables may be used to couple the laser radiation to the peripheral surgical device. Such a system may employ a Nd:YAG (Neodymium-doped yttrium aluminum garnet) laser rod 64 located between an end mirror 66 and a laser output mirror 68. The rod may be pumped by a single laser pump lamp 70. A KTP (KTiOPO4) frequency doubling crystal 72 may be employed at the required power levels to achieve frequency doubling. As shown, the KTP crystal 72 is located between an end mirror 74 and the laser output mirror 68. An acoustoptical O switch 76 may be provided to selectively quench the laser action to control the laser output. In operation the laser may be capable of producing up to 20 watts of laser radiation at a wave-length of about 532 nanometers. These output parameters make the system highly flexible and adaptable to use with a variety of peripheral medical devices.

An output laser beam 78 from the laser 52 may be coupled to a beam directing and attenuating means, or optical system 54. The beam directing and attenuating optical system 54 may include an input beam splitter and folding mirror 80 and a selectively positionable beam splitter 82 controlled by a solenoid 84. The selectively positionable beam splitter 82 provides for the selective production of a main power beam (indicated by the solid arrows 86), or a lower power aiming beam (indicated by the dotted arrows 87). Conventional rotating polarized attenuators 88 and 90 may be placed in the path of the main power beam and the aiming beam, respectively. The power of the laser radiation in the aiming beam may be reduced by lossy aiming beam reflectors 92 and 94. The main power beam or the aiming beam may be directed on a shutter 96 by means of beam splitter and folding mirror 98. When the shutter 96 is open, the power beam or aiming beam may be coupled to the optical fiber cable 60.

In operation, before the laser beam from the laser 52 enters the optical fiber cable 60, a small portion of the beam may be sampled by a beam splitter 81 and measured by a power detector 100, which is employed to measure the average output power of the laser 52. When the beam splitter 82 is moved out of the path of the laser beam, the laser beam passes to the main beam attenuator 88, which consists of two polarizing plates. Because the output beam of the laser is polarized, a rotation of the plane of incidence of the polarizing plates will attenuate the beam to a selective degree determined by the degree of rotation of the attenuator. A small motor (not shown) may be used to rotate the attenuator to produce any desired degree of attenuation. The two polarizing attenuating plates are used so that the lateral offset of the beam due to one plate is compensated by second plate. Consequently, as the attenuator is rotated, the output beam remains on axis.

Following the main beam attenuator, the main beam impinges on the beam splitter 98. A portion of the beam is directed to the second power detector 102. Ths detector monitors the power of the laser beam just before it enters the optical fiber cable 60.

The electromechanical shutter 96 is employed to block the beam on command, and is located between the beam splitter 98 and the optical fiber cable 60.

A parallel, lower power, aiming beam may be selectively derived from the output beam of the laser 52 and attenuated in a fashion similar to the main power beam just described. To produce the aiming beam the beam splitter 82 may be positioned by the solenoid 84 in the location shown in FIG. 2 to direct the laser beam toward the lossy reflector 92. From the lossy reflector 92 the aiming beam may be directed into the aiming beam attenuation 90, which operates in a fashion similar to the main power beam attenuator 88, previously described. The aiming beam may then be reflected off of lossy reflector 94 into the beam splitter 98. As in the main power beam, an average output power level of the aiming beam may be detected by the power detector 102.

The calibration pod or sensor 21 such as those known in the prior art, may be provided to calibrate the peripheral surgical devices which are selectively attached to the system. In the preferred embodiment shown in FIG. 2, the calibration sensor 21 consists of an integrating sphere 104 having an aperture 106 through which the peripheral surgical device may be inserted or its output beam directed, and a light sensitive electronic device such as a light sensitive silicon diode 108 located in a wall of the sphere. The inside surface of the sphere may be a diffusing surface as sand-blasted metal, anodized aluminum or magnesium sulfate. At any point on the surface of the sphere, the amount of illumination is essentially constant and insensitive to the exact positioning of the peripheral surgical device 58 with respect to the sensor. Sensor 21 is also referred to herein 25 sensor means.

Advantageously, the calibration sensor 21 may be removable from the console 10 and this removal detected by a proximity detector 112 which causes the system to enter its calibration mode.

As discussed above, many different peripheral surgical tools may be employed with this system. Such tools may be selectively coupled to the optical fiber cable 60. FIG. 3 is a detail of FIG. 2 showing the construction of connector portions of a peripheral surgical device and a cable emanating from the system console. The detail also illustrates the construction and function of signature resistors which may be employed in a preferred embodiment of the present invention to identify a particular peripheral surgical devices in use.

In the preferred embodiment of the present invention, signature resistors 150 may be located in a portion of peripheral surgical device 58 and provided with electrical contacts 152 by which the signature resistors are selectively connected to the control circuitry 56. The peripheral surgical device 58 may be coupled to the optical fiber cable and to a control circuitry cable 154 by means of a releasable coupling such the threaded coupling sleeves 156 and 158 shown in FIG. 3. When a shank portion of the peripheral surgical device 58 is inserted in the coupling the optical fiber cable 60 is optically coupled to the surgical device 58 and the signature resistors 150 are coupled to the control circuitry. The resistances of the signature resistors may be detected by the control circuitry, and the peripheral surgical device identified on the basis of these detected resistance. In alternative embodiments an end of the optical fiber cable from the laser may be coupled to an end of an optical fiber cable leading to the surgical device by a conventional optical coupler which focuses light from one optical fiber cable end to the other.

With continued reference to FIG. 2 the operation of the control circuitry will now be described. The control circuitry 56 may include a general purpose digital computer or special purpose microcomputer, as well as, appropriate conventional analog-to-digital and digital-to-analog converters. The control circuitry 56 receives information concerning the operation of the system from the data inputs grouped at location 200, and from a foot switch 204, the calibration mode switch 25 and switch panel 22. Control signal outputs from the control circuitry are grouped at location 202.

In operation a peripheral surgical device 58 may be selected for calibration and surgical use. The surgical device 58 may be coupled to the optical fiber cable 60 and electrical cable 154. The signature resistors in the peripheral surgical device 58 may then be interrogated to determine the identity of that particular surgical device.

The control circuitry will block the production of a laser beam by the laser optical system until the peripheral device is calibrated. The system may be switched to a calibration mode by removing the calibration sensor 21 from the console. A signal from the proximity detector 112 may be employed to trigger the control circuitry to enter a calibration mode.

The peripheral surgical device 58 may then be inserted into the sensor 21. The calibration mode switch 25 may be pressed to activate the control circuitry. At this point, a low power laser radiation pulse is produced by the system and coupled into the peripheral surgical device 58. The radiation output of the device 58 is detected by the sensor 21 and a signal representative of the power of the output beam of the peripheral surgical device 58 is communicated to the control circuitry via amplifier 113. At about the same time, power detectors 100 and 102 may produce signals representative in value of the power levels measured from the beams provided to those power detectors by the beam splitters 81 and 98. The control electronics 56 may then calculate a value representative of the ratio between the output power levels sensed by the power detectors 100 and/or 102, and the actual output power of the peripheral surgical device 58 as measured by the calibration sensor 21. Detector 100 and/or detector 102 is also referred to herein as detector means. This value may be stored for further use in an electronic memory.

When this process has been performed, the system may be enabled for surgical use with the particular peripheral device 58 which has been calibrated. Should another peripheral surgical device be coupled to the system the calibration procedure must be repeated, unless that new peripheral surgical device had been previously calibrated within a predetermined period of time, programmed into the control circuitry. By use of this system one or more peripheral surgical devices may be calibrated prior to the performance of a surgical operation. Once calibrated, the various devices may be interchanged during the operation without recalibration.

When the peripheral surgical device is used in the surgical operations, controls such as the foot switch 204 and the switch panel 22 may be employed to control the operation of the laser system. The switch panel 22 may be used to manually select desired output power levels from the peripheral surgical device 58. Of course, during a surgical operation, the real power output of the peripheral surgical device 58 cannot be conveniently measured, since such a measurement would interfere with the operation. Instead, an approximation of the actual power output level of the peripheral surgical device 58 may be calculated from the stored ratio of power outputs produced in the calibration mode and from power levels continuously detected by the power detectors 100 and 102. A feedback circuitry may be provided as indicated by arrow 208 to control the operation of the laser, to thereby adjust the output beam 78 so that the desired set point power output level is achieved. The foot-switch 204 may be employed to control the timing and/or pulse duration of the laser beam used in the surgical operation.

A video display 20 may be connected to the control circuitry to provide a display of various operating parameters of the system such as tool identity, calculated device power output level, aiming beam power output level, calibration status of the peripheral device, etc.

FIG. 4 is a schematic illustration of modes of operation of the control circuitry of the laser system embodiment described in connection with the first three figures. In the Figure, the arrows show transitions or control flow between modes, indicated generally as circles. The operations indicated in FIG. 4 may preferably be performed in a general purpose digital computer with appropriate software.

The initial system mode, the system-off mode 300, represents the state of the system when no electrical power is being applied to the apparatus. The system may be placed in the laser-off mode 302 by unlocking a key lock system. In the laser-off mode, the control electronics are activated, and the system instructs the user to press an "on" button on the control panel. By so doing, the system may be placed in the on-power up mode 304, in which the laser is brought up to power. Once the laser has reached a predetermined power level, the system may pass into the calibrate mode 306, in which the system recalls the identity of any peripheral device which is presently calibrated and displays this information on the display screen. A peripheral device will remain in a calibrated state and calibration data retained in the electronic circuitry memory for a predetermined period following system shut-down, for example, eight hours. If the system determines that one or more peripheral devices are presently calibrated, the system may pass to the standby mode 308. Removal of the calibration pod will cause the system to return to the calibration mode 306. This is also true for modes 308 through 314, now to be discussed.

In the standby mode 308, desired power and pulse timing data for the main power and/or aiming beams can be entered and modified. This data is displayed on the display screen. Power values may be displayed which are calculated from the calibration ratio and a laser output power sensed internally in the system as discussed above. To go into the ready mode 310, a ready button may be pressed which activates the foot switch or other laser pulse initiating triggers.

In a preferred embodiment, the foot switch is provided with the capability of actuating two state or mode changes: light pressure on the foot switch places the system in the aim mode 312, in which an aiming beam is produced by the system; and greater pressure on the foot switch places the system in a full power mode 314 in which a power beam is produced. The system is designed so that it must be placed in the aim mode for a predetermined short interval before going to the full power mode. This arrangement inhibits the accidental triggering of the full power beam, for example, by dropping the foot switch or accidentally stepping on the foot switch.

The standby simmer mode 316 represents a lower power mode to which the system gravitates if the system has been in the standby or ready mode, but has not been used for more than a predetermined time interval.

The system may pass to a fault 2 mode 318 from a number of the other modes as shown. In response to the detection of a type 2 fault such as an interruption in electrical or optical connections to the peripheral device. In the fault 2 mode, the production of a laser pulse is inhibited. In such a case, if a calibrated peripheral device is then connected to the system, the system will return to the standby mode 308. If an uncalibrated peripheral device is connected to the system at this point, the system will pass to the calibration mode 306.

More serious problems such as a failure of the control circuitry or a cabinet interlock malfunction may cause the system to enter the fault 1 mode 320. As shown in FIG. 4, the system may pass from the fault 1 to the laser off mode 302. Correction of the type 1 fault must be effected before the system can be again be operated in the on-power up mode.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may ne made by those skilled in the art without departing from the spirit of the invention.

What is claimed is:

1. A surgical laser apparatus comprising:
a laser operable to produce an output beam at an adjustable power level;
interchangeable peripheral surgical devices, a selected one of which is operatively coupled to the laser to receive the laser beam, said devices each having an identifying signature for use in identifying the selected device;
sensor means for sensing the power output of a surgical device coupled to the laser; and
control circuit means operatively coupled to said sensor means and to the signature of the coupled device for (a) identifying the surgical device by means of the device's signature, (b) enabling the laser to produce an output beam when the surgical device is coupled to the sensor means for measuring the power output from the device, and (c) disabling the laser from producing an output beam for surgical use until the power output of such surgical device has been measured.

2. The apparatus of claim 1 which further comprises detector means for measuring the power output from said laser, and wherein said control circuit means is operable to determine and store the ratio of the sensed power outputs from the sensor means and detector means.

3. The apparatus of claim 2 wherein said control circuit means is operable to detect the recoupling to the laser of a surgical device which was previously coupled to the laser and includes circuit means for recalling the stored value representative of said ratio.

4. The apparatus of claim 1 further comprising:
a controllable attenuator receiving output radiation from said laser; and
an optical fiber cable coupling the attenuator and the surgical device.

5. The apparatus of claim 1 wherein the sensor means comprises an integrating cavity into which the surgical device may be inserted, and a semiconductor radiation detector for receiving radiation from an interior wall of the cavity.

6. The apparatus of claim 1 wherein the signature for identifying the surgical device is an electronic resistance adapted for electrical connection with the control circuit means when the surgical device is coupled to the laser.

7. The apparatus of claim 1 further comprising beam directing and attenuating means for splitting the laser beam into a main power beam and a lower power aiming beam, and for coupling one of the main power beam and aiming beam to the surgical device.

8. The apparatus of claim 1 further comprising a two state switch operatively connected to the control circuit means for triggering the emission of laser radiation from the peripheral surgical device, said switch having a first state in which the emission of the lower power aiming beam is triggered and a second state in which the emission of the higher power main beam is triggered, wherein the control circuit means is operable to place said switch in the first state for a predetermined period of time before placing the switch in the second state.

* * * * *